US005811099A

United States Patent [19]
Ryan

[11] Patent Number: 5,811,099
[45] Date of Patent: Sep. 22, 1998

[54] METHOD AND COMPOSITION FOR PRESERVING ANTIGENS AND PROCESS FOR UTILIZING CYTOLOGICAL MATERIAL PRODUCED BY SAME

[75] Inventor: Wayne L. Ryan, Omaha, Nebr.

[73] Assignee: Streck Laboratories, Inc., Omaha, Nebr.

[21] Appl. No.: 603,740

[22] Filed: Feb. 20, 1996

Related U.S. Application Data

[62] Division of Ser. No. 240,404, May 10, 1994, abandoned, which is a continuation of Ser. No. 233,223, Apr. 26, 1994, Pat. No. 5,459,073, which is a continuation of Ser. No. 52,648, Apr. 26, 1993, abandoned, which is a continuation-in-part of Ser. No. 943,359, Sep. 10, 1992, abandoned, which is a continuation-in-part of Ser. No. 877,738, May 4, 1992, Pat. No. 5,260,048, which is a continuation-in-part of Ser. No. 696,926, May 8, 1991, Pat. No. 5,196,182.

[51] Int. Cl.$^6$ .......................... A61K 39/00; A61K 39/38; A61K 38/00; G01N 31/00
[52] U.S. Cl. .................................. 424/184.1; 424/278.1; 514/2; 514/20; 436/18
[58] Field of Search ............................ 424/184.1, 278.1; 514/2, 20

[56] References Cited

U.S. PATENT DOCUMENTS

| | | |
|---|---|---|
| 2,554,944 | 5/1951 | Ferrari . |
| 4,099,917 | 7/1978 | Kim . |
| 4,160,644 | 7/1979 | Ryan . |
| 4,219,440 | 8/1980 | Runck et al. . |
| 4,287,087 | 9/1981 | Brinkhous et al. . |
| 4,404,181 | 9/1983 | Mauthner . |
| 4,436,821 | 3/1984 | Ryan . |
| 4,493,821 | 1/1985 | Harrison . |
| 4,578,282 | 3/1986 | Harrison . |
| 4,652,449 | 3/1987 | Ropars et al. . |
| 4,666,699 | 5/1987 | Slifkin . |
| 4,704,364 | 11/1987 | Carver et al. . |
| 4,762,522 | 8/1988 | Maue . |
| 4,767,206 | 8/1988 | Schwartz . |
| 4,774,189 | 9/1988 | Schwartz . |
| 4,793,994 | 12/1988 | Helioff et al. . |
| 4,844,891 | 7/1989 | Rosent et al. . |
| 4,848,377 | 7/1989 | Bires et al. . |
| 4,867,908 | 9/1989 | Rektenwald et al. . |
| 4,876,189 | 10/1989 | Schetters et al. . |
| 4,880,602 | 11/1989 | Al-Sioufi . |
| 4,882,284 | 11/1989 | Kirchanski et al. . |
| 4,918,004 | 4/1990 | Schwartz . |
| 4,931,385 | 6/1990 | Block et al. . |
| 4,962,038 | 10/1990 | Carter et al. . |
| 4,980,176 | 12/1990 | Berke et al. . |
| 4,987,086 | 1/1991 | Brosnan et al. . |
| 5,008,201 | 4/1991 | Ryan . |
| 5,034,222 | 7/1991 | Kellett et al. . |
| 5,037,843 | 8/1991 | Schoenberg . |
| 5,059,518 | 10/1991 | Kortright et al. . |
| 5,073,623 | 12/1991 | Prantl et al. . |

(List continued on next page.)

FOREIGN PATENT DOCUMENTS

| | | |
|---|---|---|
| 0118634 | 9/1984 | European Pat. Off. . |
| 0311035 | 4/1989 | European Pat. Off. . |
| 0433516 | 6/1991 | European Pat. Off. . |
| 0469766 | 2/1992 | European Pat. Off. . |
| 2114291 | 8/1984 | United Kingdom . |
| WO 91/17436 | 11/1991 | WIPO . |
| WO 92/19951 | 11/1991 | WIPO . |
| WO 94/0629 | 3/1994 | WIPO . |

OTHER PUBLICATIONS

Downey; Contact Dermatitis, 21:54–55, 1989.
Dooms–Goossens et al; Contact Dermatitis, 14(5):322–24, 1986.
O'Brien; Aust. J. Derm; 28:36–37, 1987.
Jacobs et al, Contact Dermatitis; 33:247–254, 1995.
McCarthy, D.A. et al., "A Simple Flow Cytometric Procedure for the Determination of Surface Antigens on Unfixed Leucocytes in Whole Blood," *J. Immunol. Meth.* 163:155–160 (1993).
Eachus, K. et al., "Nitroparaffin–Derived Heterocyclic Antimicrobial Compounds," *SOFW* 9:337 342 (1991).
Tome, Y. et al., Preservation of cluster 1 small cell lung cancer antigen in zinc–formalin fixative and its application to immunohistological diagnosis, *Histopathal.* 16:469–474 (1990).
Jones, M.J. et al., Laboratory Investigations 44:32A (1981).
"Cosmetics and Drug Preservation," Kobava, J. ed., pp. 177–178, 647 and 657–659.
Histochoice™ Tissue Fixative, Clinical Lab Products (1992).
Product data sheet: TB47 Angus.
Product data sheet: TB54 Angus.
Product data sheet: TDS10 Angus.
Product data sheet: TDS28 Angus.
Product data sheet: TDS30 Angus.
Product data sheet: TDS40 Angus.
Product data sheet: TDS41 Angus.
Product data sheet: HULS.
Product data sheet: HULS Nuosept 65.
Product data sheet: HULS Nuosept 95.
Product data sheet: HULS Nuosept 145.
Keran, "Flow Cytometry in Clinical Diagnosis," pp. 311–330 (1989).

*Primary Examiner*—Nita Minnifield
*Attorney, Agent, or Firm*—Harness, Dickey & Pierce, P.L.C.

[57] ABSTRACT

A method and composition for fixing and stabilizing tissues, cells, and cell components such that the antigenic sites are preserved for a useful period of time is provided. The fixative employs a formaldehyde donor that is non-toxic, non-flammable, and that stabilizes the cell with minimal damage to and alteration of the cell morphology. The cell antigenic sites are left intact so that studies with monoclonal antibodies may be conducted. Vaccines and related immunotherapeutic methods utilizing antigens stabilized by the fixative of the present invention are also provided. The invention also discloses a method for developing a positive control for test reagents and for test instrumentation.

34 Claims, 5 Drawing Sheets

U.S. PATENT DOCUMENTS

| | | |
|---|---|---|
| 5,091,174 | 2/1992 | Lemberger . |
| 5,106,744 | 4/1992 | Kass . |
| 5,112,871 | 5/1992 | Austin . |
| 5,118,173 | 6/1992 | Donofrio et al. . |
| 5,196,182 | 3/1993 | Ryan . |
| 5,260,048 | 11/1993 | Ryan . |
| 5,262,327 | 11/1993 | Ryan . |
| 5,270,208 | 12/1993 | Ryan . |
| 5,300,424 | 4/1994 | Hoss et al. . |
| 5,459,073 | 10/1995 | Ryan . |
| 5,614,414 | 3/1997 | Ryan et al. . |

METHOD AND COMPOSITION FOR PRESERVING ANTIGENS AND PROCESS FOR UTILIZING CYTOLOGICAL MATERIAL PRODUCED BY SAME

The present application is a divisional of U.S. Ser. No. 08/240,404, filed May 10, 1994, now abandoned, which is a continuation of U.S. Ser. No. 08/233,223, filed Apr. 26, 1994, now U.S. Pat. No. 5,459,073, which is a continuation of U.S. Ser. No. 08/052,648, filed Apr. 26, 1993, now abandoned, which is a continuation-in-part of U.S. Ser. No. 07/943,359 filed Sep. 10, 1992, now abandoned, which is a continuation-in-part of U.S. Ser. No. 07/877,738, filed May 4, 1992, now U.S. Pat. No. 5,260,048, which is a continuation-in-part of U.S. Ser. No. 07/696,926, filed May 8, 1991, now U.S. Pat. No. 5,196,182. Each of the foregoing listed applications is hereby incorporated by reference in its entirety.

FIELD OF THE INVENTION

The present invention generally relates to solutions containing compositions useful in the stabilization and fixation of cells and tissues and more particularly to a composition for the stabilization and fixation of cells and tissues, that preserves antigenic sites for a useful period of time. The present invention also describes a process for stabilizing the antigenic sites of cells or cell components. The present invention further describes processes for utilizing cells or cell components for use in histological studies and the like. Also disclosed, as a further aspect of the invention, is a vaccine preparation and immunotherapeutic methods utilizing the stabilization and fixation compositions of the present invention.

BACKGROUND OF THE INVENTION

In biological and biochemical analysis, and related arts, it is often necessary to store and preserve biological tissues, such as cells, cell components, proteins, and certain organic components thereof, for useful periods of time. Such biological materials are often utilized in a wide variety of applications, including but not not limited to instructional aids and the diagnosis and treatment of diseases. For example, certain organisms and components thereof are often preserved in or by solutions for use in the learning arts. Likewise, such biological materials are often utilized in histological, cytological, immunological, and proteinaceous studies and the like.

Thus, it is desirable in the art to obtain a fixative or stabilizing solution which may be utilized to not only perform all the results obtainable by prior fixative or stabilizing solution, but to also provide a solution capable of preserving antigenic sites.

While the objects of any "preservative" utilized in fixing or stabilizing biological materials varies and depends upon the intended use of the "preserved" material, certain materials are known in the art for securing some desirable results. Thus, the present invention relates to compositions for the fixing of cells and tissues and to methods of fixing cells and tissues using as the fixing agent certain reagents.

The primary objective of tissue fixation is to provide as much structural detail of cells and components thereof as possible. To do this, it is necessary to maintain the cells in their original unaltered morphology so that maximum cellular detail may be observed. With the clinical application of immunostaining, there is also the requirement that antigens are not altered by the method of fixation or stabilization.

Although the microscope is still the conventional means for examining fixed and stained biological materials, biological materials may also be examined with a flow cytometer. The flow cytometer is an important method for examining a plurality of cells in a brief time.

The usual formulations for stabilization of cells contain one or more agents which react vigorously with the proteins of the cells to denature and insolubilize the components of the cell. Typical of this type of agent is picric acid, mercuric ions, formaldehyde and glutaraldehyde. In addition, some less toxic compounds can also be utilized which denature and stabilize the proteins such as acetic and formic acid.

Unfortunately, the toxicity associated with such compounds renders their use less than satisfactory. For example, a 37% solution of formaldehyde, the most common of these fixatives, is a noxious gas which is also toxic, flammable, and carcinogenic.

Although efforts are made when this chemical is used to protect workers and avoid contamination of the drainage system when disposed, these efforts are usually both expensive and inconvenient, and fixatives such as formaldehyde still present a danger to laboratory workers and health care professionals. Thus, it is highly desirable to develop fixatives which can be used safely, effectively and conveniently in histological studies.

Also known in the art are various methods for analyzing histological, cytological, immunological, and proteinaceous materials. For example, surface marker analysis has developed as a laboratory tool which is particularly useful for clinical diagnosis through the investigation of immunodeficiency states, differentiation of cell types and development stages, and other cell processes. The expansion of uses for surface marker analysis has resulted in the use of flow cytometry and antibody probes to evaluate cellular properties. While other means of assaying for surface marker analysis exist, flow cytometry provides rapid, objective and quantitative assessment of surface markers.

Flow cytometry and flow cytometers are generally described in Keran's text, *Flow cytometry in Clinical Diagnosis* (1989). Flow cytometers operate in principle by multiparameter analysis of heterogeneous cell populations (or cellular components) on a cell-by-cell basis. Flow cytometry allows biological and physical properties of cells and cellular components to be determined.

In flow cytometry, cells in suspension are forced single file, via hydrodynamic focusing, through the path of a laser beam. Interaction of the cells with the laser beam scatters some of the light and causes excitation and emission from fluorescent molecules present on the surface or interior of the cell. A series of lenses collect the scattered or emitted light and pass it to a photomultiplier. Each photomultiplier measures a separate parameter. Parameters measured include: forward light scatter, which measures relative particle size; side light scatter, which measures relative granularity or other internal structure; and fluorescence emission. The optical signals are converted by a computer to a data display for analysis and interpretation.

A chromophore may be applied to a cell suspension or the cells may be labeled with monoclonal antibodies which have been conjugated directly or indirectly with fluorochromes. These probes are usually specific for a surface antigen or some intracellular substance of interest, such as DNA. The choice of the probe depends on the diagnostic or biological parameter of clinical interest.

Compounds typically used to stabilize cells may preserve some cellular antigens though certain antigens are more sensitive to loss of reactivity to monoclonal antibodies. Examples of such antigens are the cluster designation antigens (CD) present on the surface of hematopoietic cells. Much of the clinically useful applications of surface marker analysis, and much of the development of the surface marker assay technology, has focused on lymphocyte CD markers.

Another problem with the use of existing compounds which stabilize cells for analysis is that certain critical antigens are present in small quantities, thus they are not detectable even if only a small percentage of these antigens are destroyed.

Therefore, it is an object of the invention to provide a fixative solution for tissues and cells which has an extremely low toxicity yet meets all of the requirements of a model fixative.

Another object of the invention is to provide a fixative solution for tissues and cells that preserves tissues and cells and their cellular detail.

Another object of the present invention is to provide a fixative which in addition to being low in toxicity gives off no noxious fumes, is not flammable or carcinogenic, and which can be disposed of safely and conveniently.

Yet another object of the invention is to provide a fixative solution for tissues and cells that preserves tissues and cells and their antigenic detail to allow for the satisfactory conducting of immunohistochemical and other immunological techniques on the tissues and cells.

Yet another object of the invention is to provide a fixative solution that provides an unaltered antigenic surface for reaction with specific antibodies for use, for example, in the preparation of vaccines and in related immunotherapeutic methods.

Yet another object of the invention is to provide cytological controls for use in biological analysis and studies. These and other objects of the invention are obtained by a fixative solution for tissues and cells comprising histological fixing amount of at least one active agent selected from the group consisting of:
i) diazolidinyl urea,
ii) imidazolidinyl urea,
iii) dimethylol-5,5-dimethylhydantoin,
iv) dimethylol urea,
v) 2-bromo-2-nitropropane-1,3-diol,
vi) 5-hydroxymethyl-1-aza-3,7-dioxabicyclo (3.3.0) octane and 5-hydroxymethyl-1-aza-3,7-dioxabicyclo (3.3.0)octane and 5-hydroxypoly[methyleneoxy] methyl-1-aza-3,7-dioxabicyclo (3.3.0)octane, and
vii) sodium hydroxymethyl glycinate.

In another aspect, the invention comprises an improvement in a method of fixing tissues and cells with a histological fixative wherein the histological fixative is an active agent selected from at least one of the group consisting of:
i) diazolindinyl urea,
ii) imidazolidinyl urea,
iii) dimethylol-5,5-dimethylhydantoin,
iv) dimethylol urea,
v) 2-bromo-2-nitropropane-1,3-diol,
vi) 5-hydroxymethyl-1-aza-3,7-dioxabicyclo (3.3.0) octane and 5-hydroxymethyl-1-aza-3,7-dioxabicyclo (3.3.0)octane and 5-hydroxypoly[methyleneoxy] methyl-1-aza-3,7-dioxabicyclo (3.3.0)octane, and
vii) sodium hydroxymethyl glycinate.

A preferred fixative solution for tissues and cells comprises histological fixing amounts of the following ingredients:

i) diazolidinyl urea,
ii) 2-bromo-2-nitropropane-1,3-diol ("Bronopol"); and
iii) a water-soluble zinc salt.

Unlike the typical histological fixing agents, the active agents of the invention have extremely low toxicity. For example, toxicity studies comparing diazolidinyl urea of the invention with formaldehyde of the prior art show the following:

|  | Inhalation Toxicity | Dermal Toxicity | LD50 |
|---|---|---|---|
| Formaldehyde | 500 mg/kg | 270 mg/kg | 800 mg/kg |
| Diazolidinyl urea | None | 2000 mg/kg | 2570 mg/kg |

This reduced toxicity makes disposal and handling less of a problem. In addition, since there is no inhalation toxicity, there are no badge detection devices required as there are for formaldehyde.

Another advantage offered by the active agents of the invention is the fact that they are not flammable and therefore do not present a fire hazard as do many of the prior art fixatives.

The mechanism by which the active agents of the invention provide the desired tissue and cell membrane stabilization is not known for certain. It is believed that the active agent binds in some fashion to the cell membrane or tissue. This hypothesis is drawn because many of the active agents of the invention are known disinfectant which kill bacteria by binding to cell structures. This is not a full explanation of the mechanism responsible for the results of the invention since many other disinfectants such as Kathon and Omadine fail to provide tissue and cell stabilizing effects.

The ability of the active agents of the invention to preserve antigens is also not understood but it is probably due to a difference in the reaction between proteins and the active agents of the invention compared to prior art fixatives such as formaldehyde. Formaldehyde cross-links with itself and proteins to obscure the antigen. To determine if this is true, diazolidinyl urea was added to the protein, albumin. After incubation of the diazolidinyl urea and protein mixture for 24 hours, disc-gel electrophoresis indicated no change in the rate of migration of the protein. When this experiment is conducted with formaldehyde, a large number of multimers and insoluble proteins result.

In another aspect of the invention, it has been found that the addition of alkali metal salts of ascorbic acid increases the activity of the active agents of the invention in fixing the tissue or cell membrane.

In yet another aspect of the invention, it has been found that the addition of glycine, or other formaldehyde reactive compound, is useful in removing any free formaldehyde which may be an equilibrium component of the compositions of the instant invention. It should be noted, however, that the preferred compositions of the instant invention contain only trace amounts of formaldehyde in equilibrium.

In yet a further aspect of the invention, it should be understood that biological material fixed or stabilized by the composition and method of the instant invention need not be stored in the composition.

It should be noted that the process for fixing biological material described in the instant specification may be practiced by those skilled in the art to preserve antigenic sites on or within cells (or components thereof derived from any source including normal blood, bone marrow, lymph, or solid tissues, or may be derived from abnormal tissues such a leukemias or solid tissue cancers. The present invention may also be utilized with any cellular component or biological material which has at least one antigenic site.

In yet a further aspect of the invention, it has been found that the fixative of the present invention may be used in the preparation of vaccines and in related immunotherapeutic methods. Thus, a vaccine comprising an antigen treated with the fixative of the present invention, in a biologically compatible form suitable for administration in vivo, and methods of administering the same to a recipient in an amount sufficient to enhance the immune response, is also provided by the present invention. Furthermore, it has been found that in vivo administration of the fixative of the present invention produces an effective immunogen, and thus a method of "boosting" an in vivo immune response in a recipient by administering the fixative of the present invention in a biologically compatible form suitable for administration in vivo, in an amount sufficient to enhance the immune response, is also provided by the present invention. By "biologically compatible form suitable for administration in vivo" is meant a form to be administered in which the toxic effects, if any, are outweighed by the therapeutic effects of the immunotherapy. Moreover, administration can be in any suitable pharmacological form, which includes but is not limited to intravenous injection.

The active reagents of the instant invention are known to be formaldehyde donors. However, while not understood, it is known that the small amount of formaldehyde held in equilibrium with the reagent is not the active mechanism of the instant compositions.

It should also be noted that in preferred embodiments of the present invention cell clumping is prevented, light scattering properties are preserved, antigenic sites are preserved, and nuclear DNA content may be analyzed.

BRIEF DESCRIPTION OF THE DRAWINGS

The various advantages of the present invention will become apparent to one skilled in the art by reading the following specification and subjoined claims and by referencing the following drawings in which:

BEST MODE FOR CARRYING OUT THE INVENTION

Figure 1:
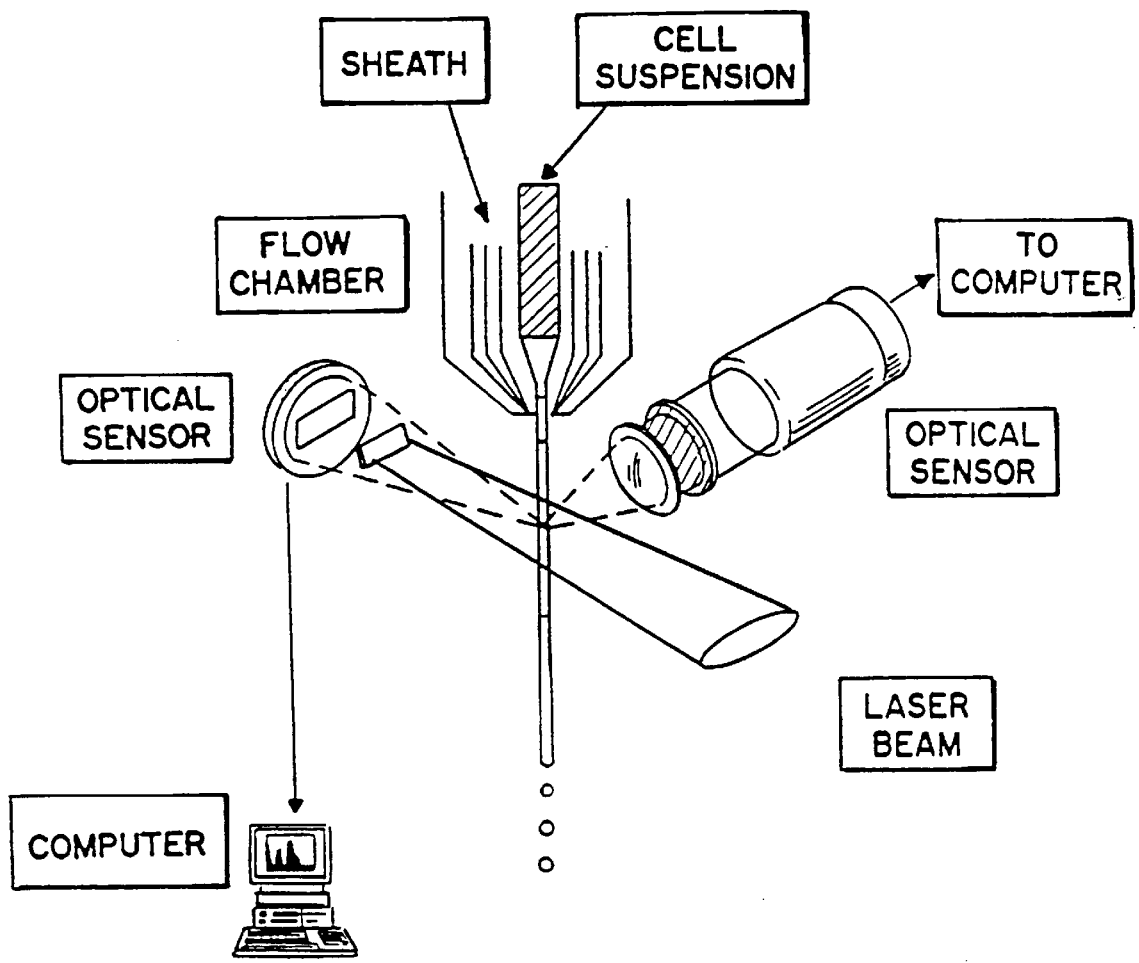
FIG. 1 is a schematic diagram of a flow cytometer.
Figure 2:
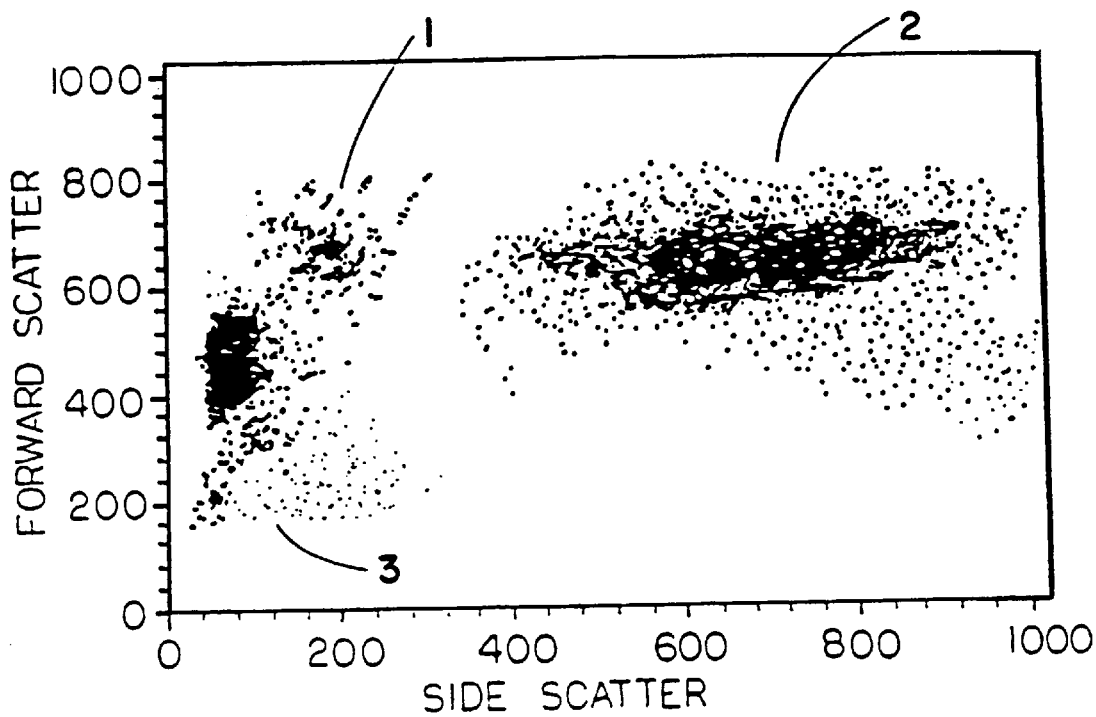
FIG. 2 is a graphical illustration of a flow cytometry scattergram wherein the enumeration of subsets is given, and wherein monocytes 1, granulocytes 2, and lymphocytes 3 are illustrated.
Figure 3:
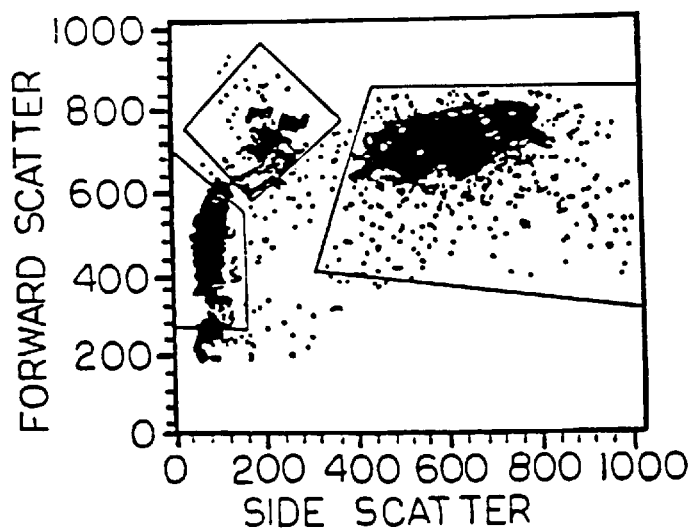
FIG. 3 is a graphical illustration of the same scattergram as illustrated in FIG. 2 wherein the subsets are "gated;"
Figure 4A:
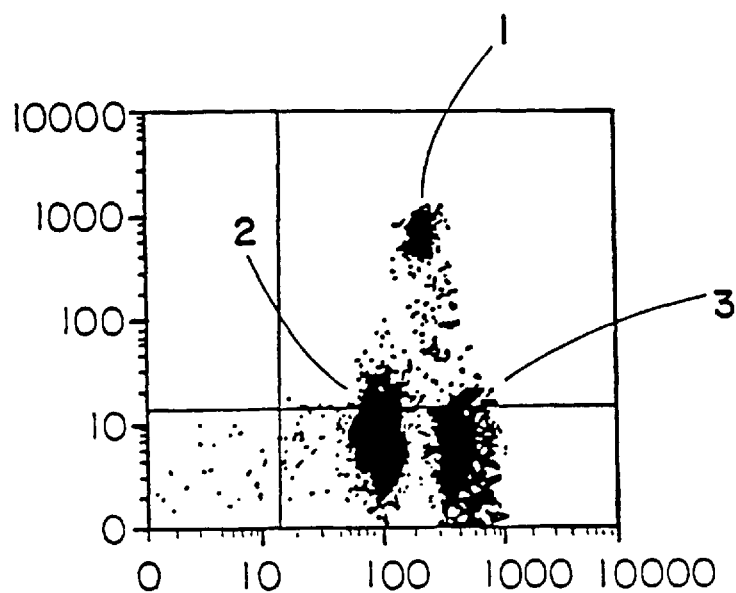
FIGS. 4A and 4B are graphical illustrations of dot plots wherein phenotyping of subsets was accomplished by means of fluorescence.
Figure 4B:
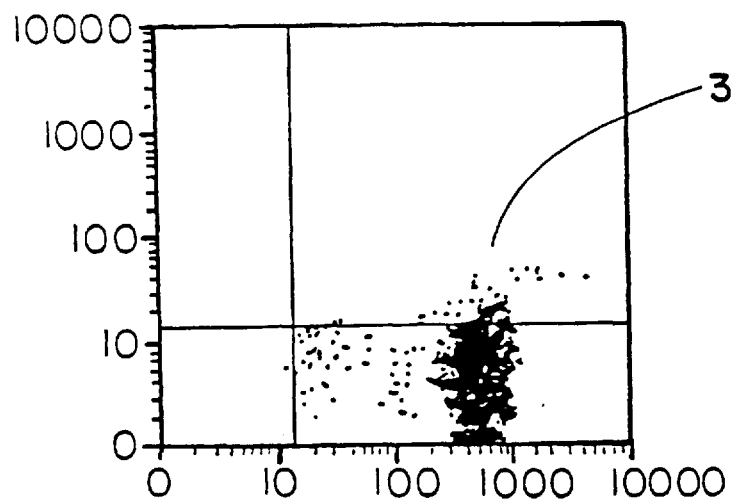
Figure 5:
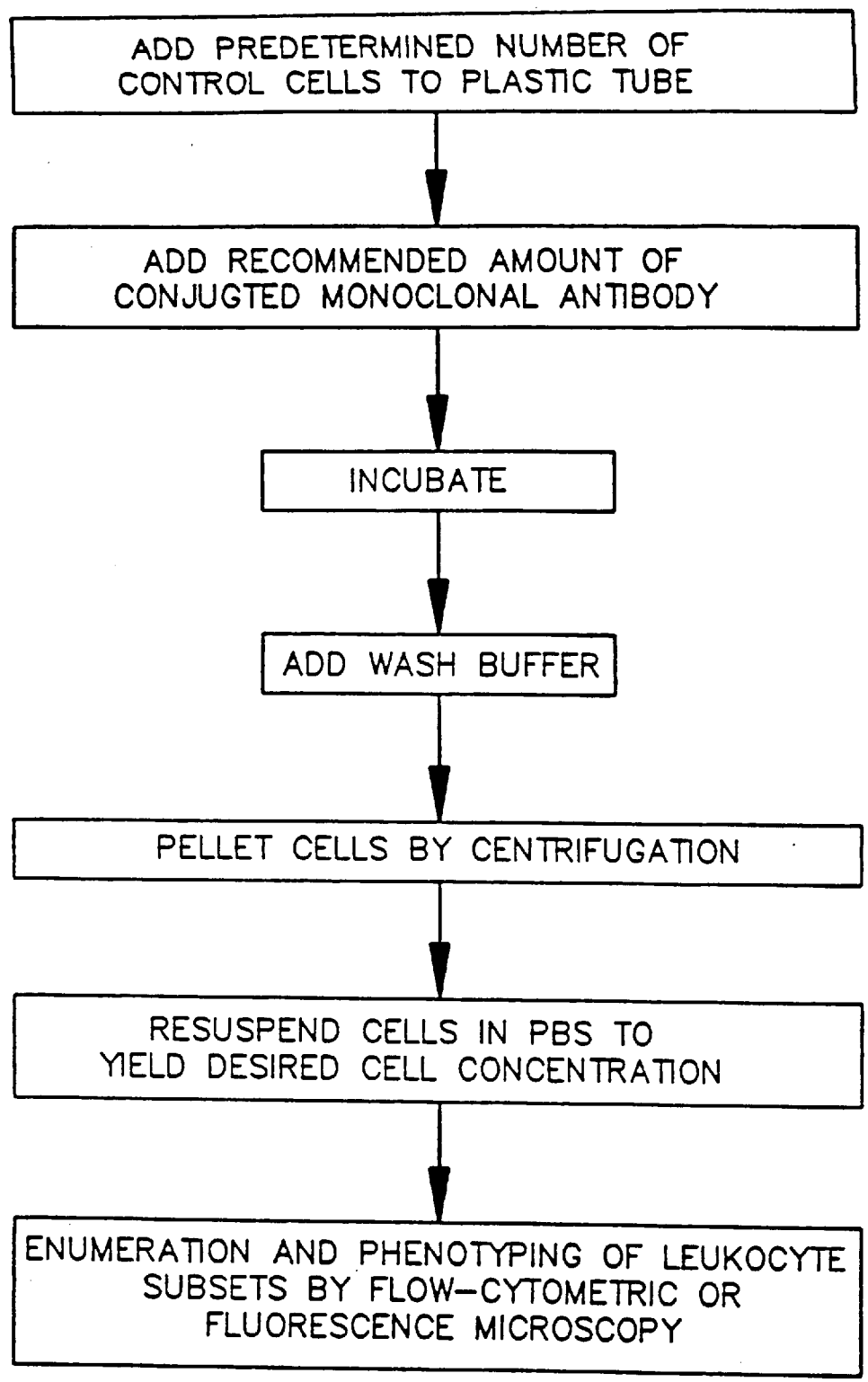
FIG. 5 is a flow diagram illustrating the procedure for preparing stabilized leukocytes for antigen-antibody studies.
Figure 6:
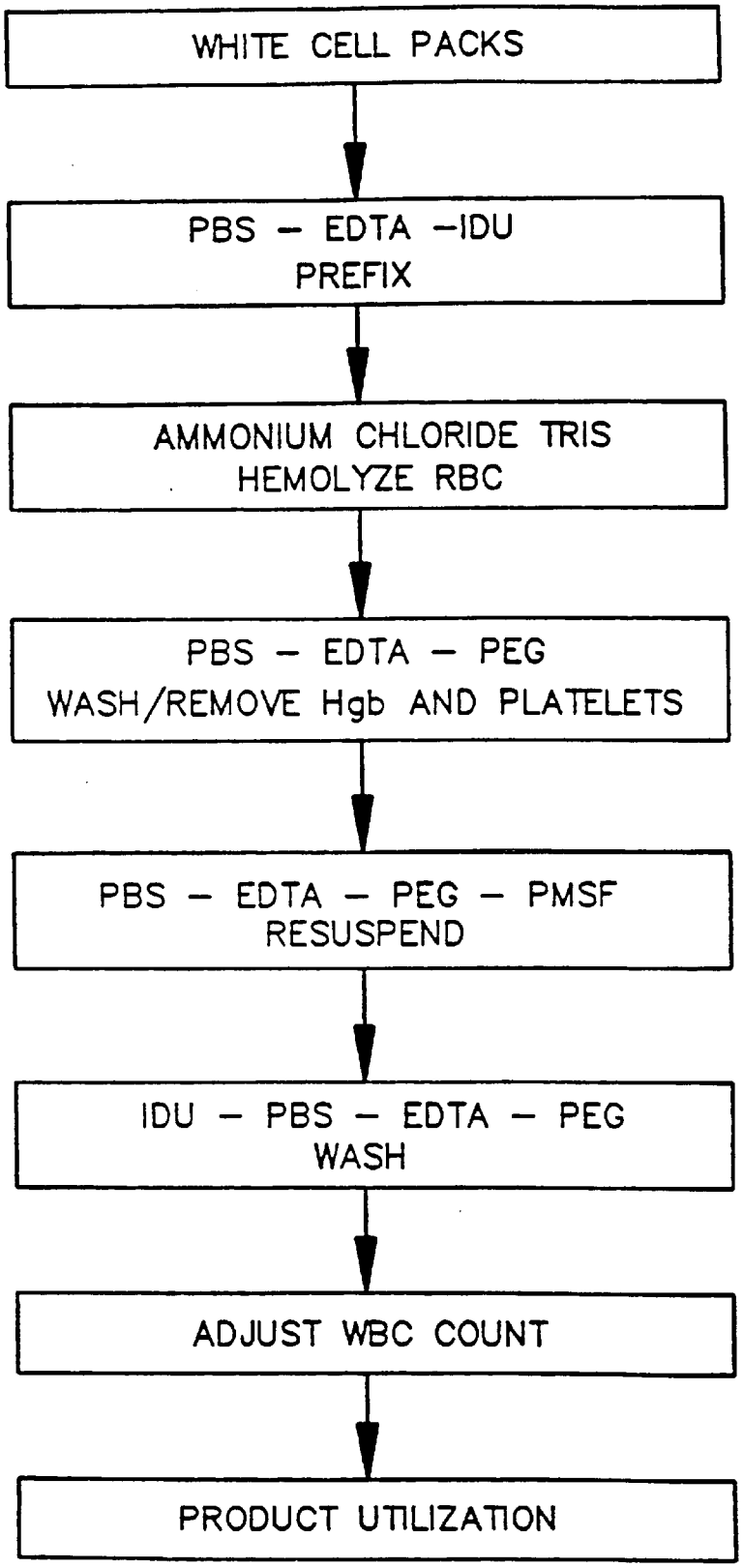
FIG. 6 is a flow diagram illustrating the procedure for preparing stabilized leukocytes subsets as a control.

The fixative solutions of the invention are comprised of the active agents in a solvent selected from water, dimethylsulfoxide, alcohol and mixtures thereof.

The alcohol solvent comprises one or more alkanols such as methanol, ethanol, propanol, butanol, polyols, e.g., diols or triols such as ethylene glycol, glycerol, propylene glycol and trimethylene glycol and mixtures of alkanols and polyols. It is also preferable that a suitable buffer such as a citrate buffer may be added to the solution to adjust the pH to about 4–6. One particularly preferred citrate buffer to be used in the solution is sodium citrate dihydrate, but other buffers may be utilized as would be obvious to one skilled in the art.

Whether the solvent employed is water, alcohol, dimethylsulfoxide, or a mixture thereof, depends principally upon the tissue or membrane being fixed. For example, where large pieces of tissue are being fixed, it is preferred to use an alcohol solvent or aqueous alcohol solvent since the alcohol solvents increase penetration. Also, in fixing cells such as Pap smears, the alcoholic preparations are preferred because they cause the cells to adhere to slides. When aqueous alcoholic solutions are employed as the solvent for the active agents of the invention, the ratio of alcohol to water will fall approximately in the range of 4:1 to 2:1.

The amount of the active agents in the formulation of the invention is that effective to fix or stabilize the tissue or cell membrane. Generally, this amount falls in the range of about 5 to 100 grams per liter, preferably 50 to 75 grams per liter. Generally, in an exemplary embodiment the compositions are comprised of about 20–40 grams of 2-bromo-2-nitropropane-1,3-diol (Bronopol) (about 30 grams particularly preferred) and about 10–15 grams of the water-soluble zinc salt (about 12 grams particularly preferred) per 1000 ml of solvent used. It is preferred that zinc sulfate, and more particularly zinc sulfate heptahydrate, be employed as the water-soluble zinc salt, but a number of other zinc salts will also be suitable as would be evident to one of ordinary skill in the art. For example, zinc salts such as zinc chloride or zinc acetate could also be employed, but these are considered less effective than zinc sulfate. In addition to the zinc salt, it is preferable to add about 2–6 grams of a citrate buffer (about 3 grams particularly preferred) such as sodium citrate dihydrate to the above fixative solution.

In terms of percentages, it is preferred that the fixative solution comprise about 1–5% Bronopol (about 3% particularly preferred). In an exemplary embodiment, about 0.02 to 0.1 g-mol/L zinc salt (about 0.05 particularly preferred) is added to the fixative solution along with the bronopol and diazolidinyl urea.

When alkali metal ascorbic acid salts such as sodium ascorbate are included to increase the activity of the active agents to fix the tissue or cells, they are added in an amount of about 0.25 to 1 grams per liter.

The solute in the preparations of the invention may also include any of the other addendum conventionally added to histological fixative preparations. These addendum include mordants, buffers, penetration increasers, osmotically active substances and nuclear detail improvers and nuclear size increasers.

Examples of suitable mordants are salt with a metal ion having an oxidation state of two or more. Illustrative are zinc, strontium calcium, barium and chromium salts. The preferred salt is zinc sulfate.

Suitable buffers include alkali metal phosphate salts such as sodium phosphate and potassium phosphate.

Osmotically active substances that may be included in the formulation of the invention are alkali metal salts such as sodium chloride. In addition, sugars such as the polysaccharides, sucrose, glucose and the like may be employed.

Nuclear detail improvers and nuclear size increasers include acetic acid and lithium salts such as lithium chloride.

Zinc salts such as zinc sulfate not only improve nuclear definition but also improve staining.

Illustrative of substances which increase the rate of penetration of the fixing agent are dimethylsulfoxide and ethanol.

In the preferred embodiment, the active fixative ingredients described above are dissolved in a suitable solvent such as distilled water, and this solution may then be used as a fixative agent in a number of ways as would be obvious to one skilled in the art. For example, the fixative solution may be used to preserve samples of tissues that are being shipped or carried to an examination site. In this process, small vials or jars that have liquid tight seals are filled with the reagent of the invention, and tissue samples are placed in the reagent-filled container to preserve the samples until they reach an area where further processing can occur.

Tissues prepared for study using the fixative of the invention may be prepared for histological study in any known conventional manner, such as through the use of paraffin sectioning equipment, staining, mounting on slides, or other common steps utilized prior to microscopic or other examination. the present invention thus provides a safe, convenient and effective fixative solution which may be utilized in the many known histological procedures that employ such solutions.

The fixative of the present invention may also be used in the preparation of vaccines. Virus and toxin vaccines, for example, which are currently prepared with formaldehyde, may be prepared by employing the fixative of the present invention. Due to the ability of the active agents of the present invention to preserve antigen integrity, vaccines employing antigens stabilized with the active agents of the present invention provide an enhanced immune response compared to antigen stabilization with currently known fixatives. It has also been shown that the active agents of the present invention may be used as an immunogen in vivo, to enhance an immune response.

The following examples are illustrative of formulations of the invention.

EXAMPLE I

| | |
|---|---|
| Diazolidinyl urea | 50 g/L |
| $Na_2HPO$ | 40.73 g/L |
| $KHPO_4$ | 0.02 g/L |
| NaCl | 8.50 g/L |
| Distilled $H_2O$ to one liter | |

EXAMPLE II

| | |
|---|---|
| Diazolidinyl urea | 50 g/L |
| Ethanol | 500 ml |
| Acetic acid, conc. | 10 ml |
| Distilled $H_2O$ to one liter | |

EXAMPLE III

| | |
|---|---|
| Diazolidinyl urea | 50 g/L |
| Lithium chloride | 6.35 g/L |
| Distilled $H_2O$ to one liter | |

EXAMPLE IV

| | |
|---|---|
| Diazolidinyl urea | 50 g/L |
| Dimethylsulfoxide | 100 ml |
| Distilled $H_2O$ to one liter | |

EXAMPLE V

| | |
|---|---|
| Diazolidinyl urea | 50 g/L |
| Dimethylsulfoxide | 100 ml |
| Zinc chloride | 5.8 g/L |
| Distilled $H_2O$ to one liter | |

EXAMPLE VI

| | |
|---|---|
| Diazolidinyl urea | 50 g/L |
| Ascorbic acid, sodium | 0.25 g/L |
| Distilled $H_2O$ to one liter | |

EXAMPLE VII

The following is an example of the use of fixatives of the invention.

Tissue is immersed in the fixative of Example I for four hours. The treated tissue is then dehydrated through a series of graded alcohols, cleared in xylene and impregnated with molten paraffin. This procedure is performed under heat and vacuum/pressure in a 12-hour cycle using a Fisher Histomatic (Model 166 MP) tissue processor. The tissue is then blocked, paraffin embedded, rehydrated in ice water for a minimum of three hours to enhance sectioning, and sectioned at 4–5 microns. The tissue is mounted on a glass slide, deparaffinized, stained, coverslipped and evaluated microscopically.

EXAMPLE VIII

The following examples demonstrates the satisfactory results obtained with the fixative of the invention using various staining methods.

Example VII is repeated using the staining method identified below. The results in each case are as follows:

| Staining Method | Results |
|---|---|
| Mayer's mucicarmine | Demonstrable; well defined |
| Elastin | Satisfactory detail |
| Movat's reticulin stain | Satisfactory detail; minimal shrinkage |
| Gomori's trichrome stain | Fibrous tissue well defined |
| Periodic Acid-Schiff (PAS) | Non-specific staining not evidenced as in formalin-fixed preparation |
| Geimsa | Satisfactory detail |
| Hematoxylin & eosin (H&E) | Satisfactory detail |

EXAMPLE IX

The following example demonstrates the ability of the fixative of the invention in retaining tissue antigens in immunostaining procedures.

The tissues identified below having the antigenic sites identified below are fixed with the fixative formulation of Example I and immunohistochemically stained using avidin-biotin staining.

| Tissue | Markers Detected |
| --- | --- |
| Lymph node | LN-1; LN-2; LN 3; UCA; L-26; LCHL-1 |
| Brain | Neurofilament; Glial Fibrillary Acidic Protein |
| Hodgkins node | Ber $H_2$; Leu $M_1$ |
| Colon | Cytokeratin MAK-6; Cytokeratin AE1/AE3 |
| Muscle | Desmin |
| Pituitary | S-100 |
| Breast | α-lactalbumin |
| Thyroid | Thyroglobulin |

EXAMPLE X

A fixative in accordance with the present invention was prepared having the following formulation:

30 grams of Bronopol; 30 grams of Diazolidinyl urea; 12 grams of zinc sulfate heptahydrate; and 2.9 grams of sodium citrate dihydrate dissolved in 1000 ml distilled water.

This solution was used as a fixative for tissue samples by placing the samples in a vial containing the fixative solution, and holding the sample for about four hours in the fixative. After the tissue has been sufficiently treated with fixative, it is then dehydrated using a series of graded alcohols, cleared in xylene and impregnated with molten paraffin. This procedure is performed under heat and vacuum/pressure in a 12-hour cycle using a Fisher Histomatic (Model 166MP) tissue processor. The tissue is then blocked, paraffin embedded, rehydrated in ice water for about three hours to enhance sectioning, and sectioned at 4–5 microns. The tissue is mounted on a glass slide, deparaffinized, stained, coverslipped and evaluated microscopically.

Through use of the composition and method of the present invention, satisfactory results have been obtained with a variety of staining methods. The following results have been obtained using the fixative of the invention:

| Staining Method | Results |
| --- | --- |
| Mayer's mucicarmine | Demonstrable; well-defined |
| Elastin | Satisfactory detail |
| Movat's reticulin stain | Satisfactory detail; minimal shrinkage |
| Gomori's trichrome stain | Fibrous tissue well-defined |
| Periodic Acid-Schiff (PAS) | Non-specific staining not evidenced as in formalin-fixed preparation |
| Hematoxylin & eosin (H&E) | Satisfactory detail |
| Geimsa | Satisfactory detail |

EXAMPLE XI

The tissues identified below having the antigenic sites identified below are fixed with the fixative formulation of Example X and immunohistochemically stained using avidin-biotin staining.

| Tissue | Markers Detected |
| --- | --- |
| Lymph node | LN-1; LN-2; LN-3; LCA; L-26; UCHL-1; B72.3 |
| Brain | Neurofilament; Glial Fibrillary Acidic Protein; Vimentin |
| Hodgkin's node | Ber $H_2$; Leu $M_1$ |
| Muscle | Desmin; Smooth Muscle Actin |
| Pituitary | S-100 |
| Thyroid | Thyroglobulin |
| Breast | α-lactalbumin; Estrogen Receptors (ER's); Progesterone Receptors (PR's) |
| Skin | HMB 45 Melanoma |
| Colon | Cytokeratin MAK-6; Cytokeratin AE1/AE3; Epithelial Membrane Ag (EMA) |

None of the antigenic sites are affected by the immunostaining.

EXAMPLE XII

Leukocyte Positive Control Check for Antigen-Antibody Studies.

Positive control methods are needed to verify the performance of reagents, preparation methods, staining procedures as well as the performance of the flow cytometer instrumentation itself. This requires a preparation of human white blood cells, preferably with a mixed distribution of leukocytes (lymphocytes, monocytes, and granulocytes), to evaluate the performance of the procedure before it is used to evaluate subject tissues, cells, or cell components. While much of the methodology used in this procedure is familiar to those skilled in the art, this invention is novel in its use of imidazolidinyl urea (IDU) as a cell stabilizer, the use of polyethylene glycol to reduce damage to the white blood cells during processing, the use of PMSF to inhibit protease activity, and the process itself.

The invention discloses a new method of producing a positive control check material with significant advances over the prior art. Production is begun by placing one pack of human white blood cells, obtainable from commercial blood banks, in each bottle of the centrifuge. Samples from each pack are placed into a plastic tube for screening on the flow cytometer. Because of the considerable variation from donor to donor in cluster designation antigen sites, only packs with similar properties are pooled. Each product pool should be limited to a particular ABO blood type to prevent clumping as a result of a histo-incompatibility reaction between the cells. The samples are placed into plastic tubes rather than glass because unfixed white blood cells may be activated by the glass causing them to adhere to the glass and each other.

The cells are prefixed 1:1 with 1% IDU in phosphate buffered saline ethylenediaminetetraacetic acid (PBS-EDTA) at 6° C. for one hour. This acts to stabilize the white blood cells without interfering with the lysis of the red blood cells. The cells and all diluents used in the processing must be kept at 6° C. at all times by use of refrigeration and a chiller bath to reduce the amount of cell damage which alters the scattergram.

The bottles are next centrifuged at 900 rpm for 10 minutes, and the supernatant is removed. This angular velocity is sufficient to pellet the white blood cells without damaging them. Ammonium chloride tris, 200 ml/bottle set at 6° C. for 20–30 minutes, is then used to lyse the red blood cells.

A second centrifugation follows, again at 900 rpm for 10 minutes and then the supernatant is removed. Next 250 ml/bottle of ammonium chloride tris are added at 6° C. or 45–60 minutes, with 60 minutes usually ensuring complete lysis of the red blood cells.

The material is then centrifuged a third time at 900 rpm for 10 minutes and then the supernatant is removed. If the cell pellets still contain red blood cells, add 150 ml/bottle of ammonium chloride tris at 6° C. for 20 to 30 minutes and centrifuge a fourth time at 900 rpm for 10 minutes and remove the supernatant.

The cells are then washed three times with PBS/EDTA/ 1% polyethylene glycol (PEG) 20,000 by centrifuging at 900 rpm for 10 minutes and removing the supernatant.

After the final wash, each bottle is resuspended with 100 ml of PBS/EDTA/0.3% PEG/3% IDU/2 mM phenylmethylsulfonyl fluoride (PMSF) and set at 6° C. for 2 days. Fixation with 3% IDU stabilizes the cells for use on the flow cytometer, with lower concentrations of IDU reducing stability and higher concentrations causing cells to lose the cluster designation marker and produce scatterplot changes. Next each bottle is washed two times with PBS/EDTA/0.3% PEG/3% IDU to remove PMSF and residual platelets.

Finally, the white blood cell count of each bottle selected for final pooling should be adjusted to meet the final product specifications. These counts may be performed on the ELT 1500 or ZBI, in triplicate, prior to pooling.

The product is now ready for use in aiding laboratory studies in that a desired reagent may be combined with the product and then examined with a flow cytometer to establish a normal baseline for the evaluation of subject tissue, cells, and cell components.

The product prepared according to this procedure may be utilized to analyze more antibodies since it contains lymphocytes, monocytes, and granulocytes. Thus, the product of this process is more complete control and all WBC's produce a scattergram similar to that of whole blood.

Product produced by the before mentioned procedure has a seven day open vial stability, does not have to be reconstituted, is compatible with all major flow cytometry systems, and one product may be utilized to monitor several areas of quality control.

The present invention has several advantages over prior art controls. For example, the prior art controls: (1) do not resemble human specimens, i.e., size, shape and granularity; (2) have short open vial stability (24 hours); (3) are lyophilized and must be reconstituted; and (4) cannot be utilized to test lyse procedures.

EXAMPLE XIII
Indirect Immunofluorescence Staining of Cell Surfaces.

The indirect method of immunofluorescence staining of cell surfaces may be used to enhance the fluorescence signal, and may also be utilized with the present invention to enhance its function as a positive control check. Since indirect methods will alter the proportionality between the amount of antigen and the fluorescence intensity per cell, these methods are not recommended for assessing the absolute number of antigenic determinants per cell, but are effective in determining the relative quantitative differences between control and subject cell populations.

EXAMPLE XIV
Direct Immunofluorescence Staining of Cell Surfaces.

This method is used to detect cells bearing specific membrane antigens by treating a cell population with monoclonal antibodies conjugated to fluorescein or phycoerythrin, and is recommended for analysis by flow cytometry or fluorescence microscopy. The use of the present invention control procedure is ideally suited to the direct immunofluorescence staining method in establishing a quality control program for laboratory reagents, procedures, and flow cytometers.

EXAMPLE XV
Immunotherapy.

Tumor specific antigens appear labile and current research suggests that antigens must be presented to the immune system while on the tumor cell. Thus, studies to determine whether tumor cells could be stabilized by the fixative of the present invention to produce an effective tumor specific antigen were performed.

6C3HED lymphosarcoma (obtained from NCI) was grown in C3H mice (purchased from Jackson Labs) as ascites (ascites cause collection of fluid in the peritoneal cavity and death in about 18–21 days). The ascites cells were then washed in phosphate buffered saline (PBS) containing 3% IDU or 3% Glydant or 3% Dimethylol urea. It will be appreciated by those skilled in the arts that any appropriate diluent such as water may also be used. The cells were then placed at 6° C. for 48 hours. Vital staining indicated that none of the cells were viable. The tumor cells stabilized with the above fixatives can be stored for at least four months without loss of effectiveness as a vaccine.

As a control for immunization, cells were then washed into PBS containing 3% para formaldehyde and held under the same conditions. After 48 hours, all the cell groups were washed into PBS to remove the fixatives. The cell count was adjusted to 200,000/ml. Five C3H mice were injected intraperitoneally with $2-5 \times 10^6$ cells of each of the cell groups for the first immunization. The procedure was repeated two weeks later.

The immunized mice were challenged with $2 \times 10^6$ viable 63HED ascites cells by intraperitoneal injection. The efficacy of the immunization was determined by the average death time for each group of mice.

Average Death Days

| | | |
|---|---|---|
| A. | Control | 18 days |
| B. | IDU | No deaths at 65 days |
| C. | Glydant | No deaths at 65 days |
| D. | Dimethylol urea | No deaths at 65 days |

This experiment was repeated several times with variations in timing and dosage. In every instance the immunized mice survived (100%) and the control mice died (100%).

To determine if a therapeutic response can be obtained, the mice were also injected with the tumor challenge, i.e. $2 \times 10^6$ viable 63HED ascites cells, first and then immunized later. By using this protocol, it was possible to protect 50% of the mice i.e. 50% of the mice lived. The mice that were immunized and died lived an average of 40 days (death usually occurs at 18–21 days). It is thus evident that even under these circumstances, protection is conferred.

The possible effect of IDU on tumor cells in vivo was also studied. Live tumor cells were injected intraperitoneally into the mice. After three days, an intraperitoneal injection of IDU was given. This was repeated two more times at three day intervals.

At 7.5 mg/mouse IDU, all of the untreated (control) mice died. 30% of the treated mice survived. The average death time for the treated mice that died was 41 days. At 15 mg/mouse IDU, all of the control mice died. The treated mice all survived and small tumors developed which regressed in about two to three days. At 30 mg/mouse IDU, all of the control mice died and all of the treated mice survived. The treated mice were also held for three months to determine if the tumor would recur. No tumors appeared. Based on these findings, it is believed that the IDU is binding with the tumor cells in vivo to produce an effective immunogen.

Studies utilizing tetanus toxin treated with the fixative of the present invention were also performed. Tetanus toxin must be treated before it can be used to immunize and presently this is done with formalin. In order to compare formalin and the fixative of the present invention, Swiss mice were inoculated intraperitoneally with tetanus toxin prepared by inactivation with IDU or formalin. Although the level of IDU used can be 1% or greater, for this experiment, a 5% solution (final) was used to inactivate the toxin. The antibody levels were then measured at 14 and 28 days.

|     | 14 Days | 28 Days |
| --- | --- | --- |
| IDU | 200 | 560 |

These values set forth the percent increase in antibody titer over formalin.

It should be noted that the concentration range for the active ingredient is best established in order to preserve antigenic sites by setting a low-end which preserves the cell or protein and also preserves the physical properties of cell size and granularity. The upper-end is set so as to preserve the antigenic sites and provide reproducible results over time.

General Information

A 6% w/v solution of each compound was used and samples tested at 24 hours (22° C.). Relative RBC fixation was detected by adding known RBC lysing agent. WBC's are fixed if these cells do not disintegrate or clump over a period of approximately two hours after removal of compound. Fixing is relative and depends on how long you want cells or tissues to remain fixed. Structures:

1) Bronopol: 2-bromo-2-nitropropane-1, 3-diol. Synthesized from p-formaldehyde and nitromethane, then bromated. Decomposition liberates formaldehyde. Fixes both RBC's and WBC's.

2) Imidazolidinyl urea: Synthesized by reaction of allantoin and formaldehyde. Decomposition releases formaldehyde. Fixes both RBC's and WBC's.

3) Diazolidinyl urea: Synthesized by reaction of allantoin and formaldehyde. Contains 1–2 ppm of formaldehyde. Fixes both RBC's and WBC's.

4) Glydant: Dimethylol-5, 5-dimethylhydantoin, a formaldehyde derivative. solution contains 2.1% formaldehyde. Fixes both RBC's and WBC's.

5) Dimethylol urea: Synthesized from urea and formaldehyde. formaldehyde is released in very small quantities. Fixes both RBC's and WBC's.

6) NuoSept 95: Synthesis not known. Contains:
    a) 5-hydroxymethyl-1-aza-3, 7-dioxabicyclo (3.3.0) octane,
    b) 5-hydroxymethyl-1-aza-3,7-dioxabicyclo (3.3.0) octane,
    c) 5-hydroxypoly[methyleneoxy]methyl-1-aza-3,7-dioxabicyclo (3.3.0)octane. Fixes both RBC's and WBC's.

7) Suttocide: Sodium hydroxymethyl glycinate. Derivative of glycine. Fixes both RBC's and WBC's. Contains 1% formaldehyde.

All of the disinfectants described as cell fixatives or stabilizers may be used to fix cells or tissues. The concentration and additives ($ZnSO_4$, ethylene glycol, etc.) will vary depending upon the circumstances of use. The characteristics of all of the above disinfectant compounds are:

a) they contain formaldehyde as an equilibrium component,
b) they can be synthesized from formaldehyde,
c) they are chemical disinfectants,
d) they are capable of undergoing hydrogen bonding, and
e) they function to fix or stabilize at concentrations two to ten times their usual concentration as a bactericide.

Our studies with cells indicates fixing and stabilizing activity is not due to free formaldehyde, ie., when compounds which react readily with the free formaldehyde are added, the tissue fixation still occurs. Example of these formaldehyde reactive compounds are glycine, allantoin, and sulfites.

Whereas, the invention has been described in connection with preferred embodiments and procedures thereof, it is apparent that many additions, modifications and substitutions may be made which are within the intended broad scope of the appended claims.

Thus, there has been shown and described an improved composition, method, and process which accomplishes at least all of the stated objects.

We claim:

1. A vaccine comprising;
   (a) an antigen wherein the antigen has been treated with an active agent selected from the group consisting of:
      i) diazolidinyl urea,
      ii) imidazolidinyl urea,
      iii) dimethylol-5,5-dimethylhydantoin,
      iv) dimethylol urea,
      v) 2-bromo-2-nitropropane1,3-diol,
      vi) 5-hydroxymethyl-1-aza3,7-dioxabicyclo (3.3.0) octane and 5-hydroxymethyl-1-aza-3,7-dioxabicyclo (3.3.0octane and 5-hydroxypoly[methyleneoxy] methyl-1-aza-3,7-dioxabicyclo (3.3.0)octane,
      vii) sodium hydroxymethyl glycinate, and mixtures thereof; and
   (b) a pharmaceutically acceptable carrier.

2. The vaccine of claim 1, wherein the active agent is diazolidinyl urea.

3. The vaccine of claim 1, wherein the active agent is imidazolidinyl urea.

4. The vaccine of claim 1, wherein the active agent is dimethylol-5,5-dimethylhydantoin.

5. The vaccine of claim 1, wherein the active agent is dimethylol urea.

6. The vaccine of claim 1, wherein the active agent is 2-bromo-2-nitropropane-1,3-diol.

7. The vaccine of claim 1, wherein the active agent is 5-hydroxymethyl-1-aza-3,7-dioxabicyclo (3.3.0)octane and 5-hydroxymethyl-1-aza-3,7-dioxabicyclo (3.3.0)octane and 5-hydroxypoly[methyleneoxy]methyl-1-aza-3,7-dioxabicyclo (3.3.0)octane.

8. The vaccine of claim 1, wherein the active agent is sodium hydroxymethyl glycinate.

9. The vaccine of claim 1, wherein the active agent is in a solution.

10. The vaccine of claim 9, wherein the solution further comprises saline.

11. The vaccine of claim 9, wherein the solution further comprises water.

12. The vaccine of claim 9, wherein the active agent is present in an amount of about 5 to about 100 grams per liter.

13. A method of enhancing an immune response in a recipient, comprising the steps of:
    a) treating an antigen to which an enhanced immune response thereto is desired with an active agent selected from the group consisting of:

i) diazolidinyl urea,
   ii) imidazolidinyl urea,
   iii) dimethylol-5,5-dimethylhydantoin,
   iv) dimethylol urea,
   v) 2-bromo-2-nitropropane-1,3-diol,
   vi) 5-hydroxymethyl-1-aza-3,7-dioxabicyclo (3.3.0) octane and 5-hydroxymethyl-1-aza-3,7-dioxabicyclo (3.3.0)octane and 5-hydroxypoly[methyleneoxy]methyl-1-aza-3,7-dioxabicyclo (3.3.0)octane,
   vii) sodium hydroxymethyl glycinate, and mixtures thereof; and
b) administering the treated antigen in a biologically compatible form suitable for administration in vivo to the recipient in an amount sufficient to enhance the immune response to the antigen.

14. The method of claim 13, wherein the active agent is diazolidinyl urea.

15. The method of claim 13, wherein the active agent is imidazolidinyl urea.

16. The method of claim 13, wherein the active agent is dimethylol-5,5-dimethylhydantoin.

17. The method of claim 13, wherein the active agent is dimethylol urea.

18. The method of claim 13, wherein the active agent is 2-bromo-2-nitropropane-1,3-diol.

19. The method of claim 13, wherein the active agent is 5-hydroxymethyl-1-aza-3,7-dioxabicyclo (3.3.0)octane and 5-hydroxymethyl-1-aza-3,7-dioxabicyclo (3.3.0)octane and 5-hydroxypoly[methyleneoxy]methyl-1-aza-3,7-dioxabicyclo (3.3.0)octane.

20. The method of claim 13, wherein the active agent is sodium hydroxymethyl glycinate.

21. The method of claim 13, wherein the active agent is in a solution.

22. The method of claim 21, wherein the solution further comprises saline.

23. The method of claim 21, wherein the solution further comprises water.

24. The method of claim 13, wherein the active agent is present in an amount of about 5 to about 100 grams per liter.

25. A method of boosting an in vivo immune response in a recipient, comprising the steps of:

a) treating an antigen to which a boosted in vivo immune response thereto is desired with a solution comprising at least one active agent selected from the group consisting of:
   i) diazolidinyl urea,
   ii) imidazolidinyl urea,
   iii) dimethylol-5,5-dimethylhydantoin,
   iv) dimethylol urea,
   v) 2-bromo-2-nitropropane-1,3-diol,
   vi) 5-hydroxymethyl-1-aza-3, 7-dioxabicyclo (3.3.0) octane and 5-hydroxymethyl-1-aza-3, 7-dioxabicyclo (3.3.0)octane and 5-hydroxypoly[methyleneoxy]methyl-1 -aza-3,7-dioxabicyclo (3.3.0)octane,
   vii) sodium hydroxymethyl glycinate, and mixtures thereof; and
b) administering the solution in a biologically compatible form suitable for administration in vivo to the recipient in an amount sufficient to boost the immune response.

26. The method of claim 25, wherein the active agent is diazolidinyl urea.

27. The method of claim 25, wherein the active agent is imidazolidinyl urea.

28. The method of claim 25, wherein the active agent is dimethylol-5,5-dimethylhydantoin.

29. The method of claim 25, wherein the active agent is dimethylol urea.

30. The method of claim 25, wherein the active agent is 2-bromo-2-nitropropane-1,3-diol.

31. The method of claim 25, wherein the active agent is 5-hydroxymethyl-1-aza-3,7-dioxabicyclo (3.3.0)octane and 5-hydroxymethyl-1-aza-3,7-dioxabicyclo (3.3.0)octane and 5-hydroxypoly[methyleneoxy]methyl-1-aza-3,7-dioxabicyclo (3.3.0)octane.

32. The method of claim 25, wherein the active agent is sodium hydroxymethyl glycinate.

33. The method of claim 25, wherein the solution further comprises water.

34. The method of claim 25, wherein the solution further comprises saline.

* * * * *

UNITED STATES PATENT AND TRADEMARK OFFICE
CERTIFICATE OF CORRECTION

PATENT NO. : 5,811,099
DATED : September 22, 1998
INVENTOR(S) : Wayne L. Ryan

It is certified that error appears in the above-identified patent and that said Letters Patent is hereby corrected as shown below:

ON THE TITLE PAGE please insert the following information:

--Notice: The term of this patent shall not extend beyond the expiration date of Pat. No. 5,459,073--.

Column 1, line 42, delete "not" (second occurrence in patent).

Column 4, line 64, after "thereof" insert --)--.

Column 14, line 31, claim 1, "aza3" should be --aza-3--.

Column 14, line 33, claim 1, "(3.3.Ooctane" should be --(3.3.0)octane--.

Column 7, line 23, "the" should read --The--.

Signed and Sealed this

Tenth Day of August, 1999

Attest:

Q. TODD DICKINSON

*Attesting Officer*  *Acting Commissioner of Patents and Trademarks*